United States Patent [19]
Tseng et al.

[11] Patent Number: 5,779,471
[45] Date of Patent: Jul. 14, 1998

[54] DELIVERY OF SUBSTANCE TO THE MOUTH

[75] Inventors: Mingchih M. Tseng, Hingham; Jean L. Spencer, Boston, both of Mass.; Thomas Craig Masterman, Foster City, Calif.

[73] Assignee: Gillette Canada Inc., Kirkland, Canada

[21] Appl. No.: 594,694

[22] Filed: Jan. 31, 1996

Related U.S. Application Data

[63] Continuation-in-part of Ser. No. 400,611, Mar. 8, 1995, abandoned.

[51] Int. Cl.$^6$ ................................................. A61C 17/02
[52] U.S. Cl. ............................................ 433/80; 433/88
[58] Field of Search .............................. 433/80, 81, 89, 433/88, 215; 601/162; 604/84

[56] References Cited

U.S. PATENT DOCUMENTS

| | | | |
|---|---|---|---|
| 3,699,979 | 10/1972 | Muhler et al. | |
| 3,934,001 | 1/1976 | Watson | 424/49 |
| 3,943,949 | 3/1976 | Ashton et al. | |
| 3,957,964 | 5/1976 | Grimm, III | 424/10 |
| 4,033,365 | 7/1977 | Klepak et al. | |
| 4,348,378 | 9/1982 | Kosti | 424/7 |
| 4,668,190 | 5/1987 | Overmyer | 433/80 |
| 4,685,883 | 8/1987 | Jernberg | 433/215 |
| 4,780,320 | 10/1988 | Baker | 424/497 |
| 4,837,007 | 6/1989 | Duckworth | 424/52 |
| 4,892,736 | 1/1990 | Goodman | 424/443 |
| 4,919,939 | 4/1990 | Baker | 424/493 |
| 4,941,459 | 7/1990 | Mathur | 433/88 |
| 4,961,698 | 10/1990 | Vlock | 433/86 |
| 4,975,054 | 12/1990 | Esrock | 433/80 |
| 4,978,391 | 12/1990 | Jones | 433/208 |
| 4,979,503 | 12/1990 | Chernack | 433/88 |
| 4,980,150 | 12/1990 | Keith | 424/49 |
| 5,061,106 | 10/1991 | Kent | 401/268 |
| 5,062,795 | 11/1991 | Woog | 433/80 |
| 5,087,198 | 2/1992 | Castellini | 433/80 |
| 5,098,711 | 3/1992 | Hill et al. | 424/401 |
| 5,186,625 | 2/1993 | Bailey | 433/88 |
| 5,218,956 | 6/1993 | Handler et al. | 604/19 |
| 5,220,914 | 6/1993 | Thompson . | |
| 5,230,624 | 7/1993 | Wolf et al. | 433/82 |
| 5,393,228 | 2/1995 | Policicchio | 433/88 |

FOREIGN PATENT DOCUMENTS

| | | |
|---|---|---|
| 0244118 | 4/1987 | European Pat. Off. . |
| 2624721 | 6/1989 | France . |
| 28 47 247 | 5/1980 | Germany . |
| 3322716 | 1/1985 | Germany . |
| 90 14 520 | 2/1995 | Germany . |

*Primary Examiner*—Cary E. O'Connor
*Attorney, Agent, or Firm*—Fish & Richardson P.C.

[57] ABSTRACT

A method of introducing a substance into a mouth, including flowing water into contact with a composite and then into the mouth, the composite including a substance that is released from the composite when water contacts the composite, the substance being released from the composite when contacted with the flowing water and carried by the flowing water into the mouth.

59 Claims, 2 Drawing Sheets

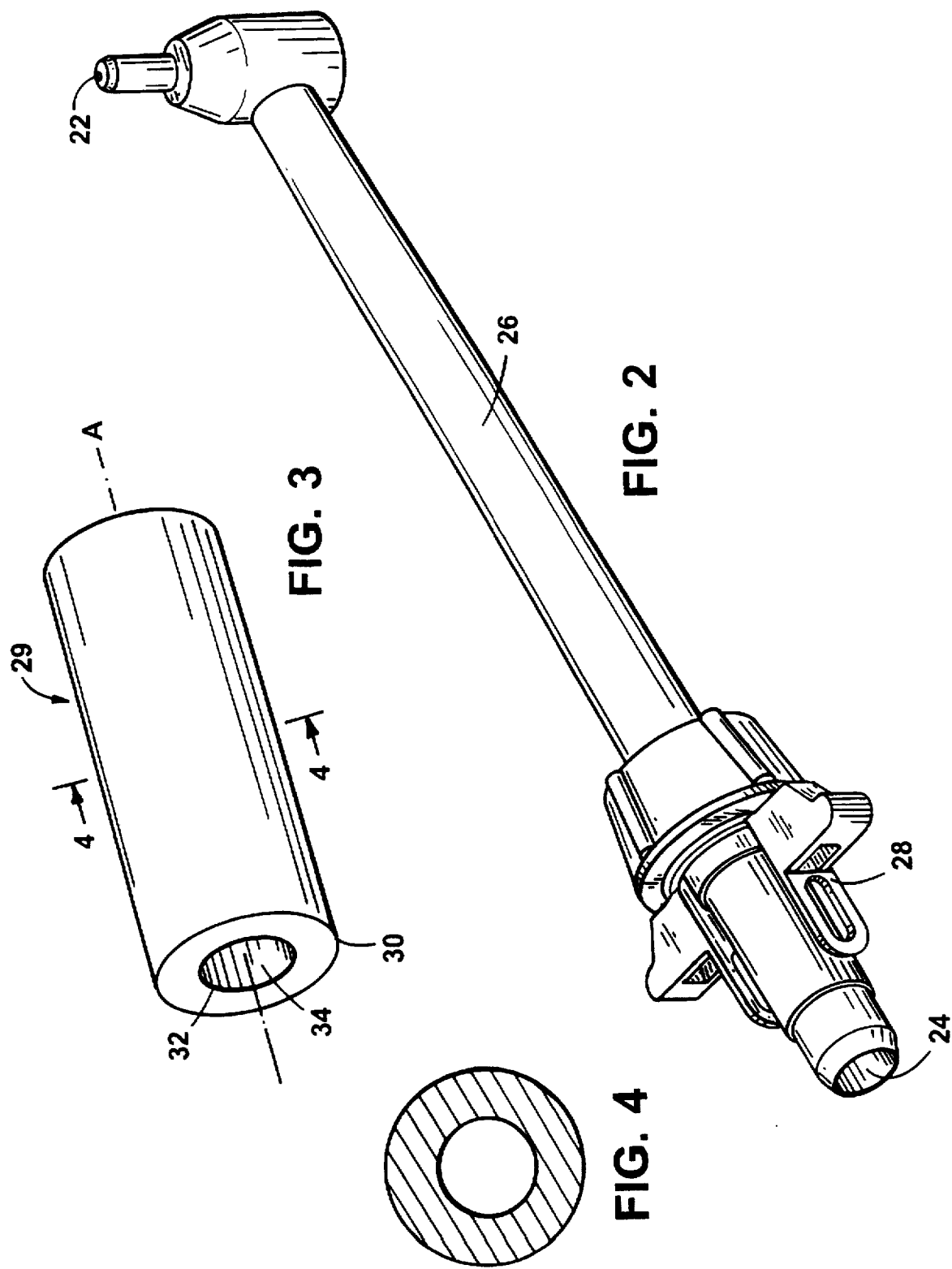

DELIVERY OF SUBSTANCE TO THE MOUTH

This is a continuation-in-part of application Ser. No. 08/400,611, filed Mar. 8, 1995, now abandoned.

FIELD OF THE INVENTION

The invention relates to the delivery of a substance into the mouth.

BACKGROUND OF THE INVENTION

Tooth decay and periodontal disease are common problems caused by bacteria and plaque present in the mouth. Reducing decay-causing bacteria and plaque has long been the target of persons working in the health care field. The most common way to reduce bacteria is to brush and floss the teeth regularly and to visit a dental hygienist to have the teeth and gums cleaned regularly.

Oral irrigation systems are known in the dental field. Dentists and oral hygienists have long used oral irrigation systems for lavage, tissue stimulation and oral rinsing. More recently, home versions of oral irrigation systems have become available for everyday use. Most oral irrigation systems for home use require the use of water. By forcing water through a hand-held tip, a jet stream is created which removes food particles from between the teeth, while also stimulating and massaging the gums.

Antimicrobial agents (sometimes called antibacterial agents) are known for treatment of plaque and decay-promoting bacteria.

SUMMARY OF THE INVENTION

The invention relates to delivering a selected substance to the mouth. The substance can be, for example, an antimicrobial agent, a whitener, a flavoring, a fluoride compound, a foaming agent, a desensitizing agent, a nutritional agent, an odor-preventing agent, a remineralizing agent, an anti-calculus agent, an anti-inflammatory agent, a salivary gland stimulator, an antifungal agent, or an antiviral agent. The invention uses a composite including the substance, and is designed so that the substance is released from the composite when the composite is contacted with water.

There are a number of aspects to the invention.

One aspect features an oral irrigator for delivering a substance to the mouth when water flows through the irrigator. The irrigator includes a tip portion for delivering water into the mouth, a flow path that delivers water through the irrigator, including the tip, and a composite that includes a substance that is released when the composite is contacted with water. The composite preferably is molded or extruded, and is positioned in the irrigator so that water flowing through the irrigator contacts the composite. As a result, during use of the irrigator the substance leaches out of the composite into the water and is carried into the mouth.

A preferred composite includes a water-insoluble polymer that functions as a support resin, a water-soluble polymer (e.g., polyethylene oxide or polyacrylic acid), and the substance. Alternatively, a water-swellable polymer or a water-soluble monomeric species may be used instead of or in addition to the water-soluble polymer. The water-soluble material enhances the release of the substance from the composite because the material dissolves from the composite when the composite is contacted with water, causing channels to form in the composite through which the substance can leach into the water. The water-swellable material absorbs water and swells, enhancing the release of the substance from the composite. Thus, both water-soluble materials and water-swellable materials facilitate release of the substance from the composite into the flow path.

Another preferred composite includes a water-soluble polymer (e.g., polyethylene oxide or polyacrylic acid) and the substance.

A preferred composite is tube-shaped and has a central opening through which water can pass.

In another aspect, the invention features a tip that is suitable for attachment to an oral irrigator. The tip includes one of the composites described above.

In another aspect, the invention features a method of introducing a substance into the mouth. The method includes flowing water over a composite including the substance, and then into the mouth. The substance is released into the water and delivered to the mouth.

In another aspect, the invention features an oral irrigator or tip for an oral irrigator that includes a solid composition including a bisguanide such as chlorhexidine or alexidine, or a quaternary ammonium salt such as cetyl pyridium chloride, that acts as an antimicrobial agent. The composition is positioned in the irrigator or tip so that water flowing through the irrigator contacts the composition, causing the release of the bisguanide into the water and, ultimately, into the mouth. The invention also features using the oral irrigator or tip to deliver the bisguanide or quaternary ammonium salt to the mouth.

The invention provides a simple way to deliver a wide variety of substances to the mouth. The composites are easy to manufacture. They can, for example, be co-extruded or two-color molded along with the tip or other portion of the irrigator. Alternatively, the composites can be extruded or molded to a shape suitable to fit, for example, at any point along the flow path in an oral irrigator. The composite can be inserted permanently into the irrigator during manufacture, or the composite can be sized and shaped so that a user can insert or remove it from the irrigator. In the latter embodiment the user can simply replace a used composite with a new composite when necessary. Also, when the irrigator includes a replaceable tip and the composite is included in the tip, the tip may be replaced when the original composite is used up. Alternatively, the composite may include a component that when released along with the substance causes a color change in the composite.

The composite including a water-soluble material in particular can be designed to release a targeted dosage of a substance when the composite contacts water. The rate of release of the substance from the composite can be adjusted by varying the quantity of the substance and the water-soluble material in the composite. The more substance and/or water-soluble material in the composite, the higher the rate of release. Release can also be controlled by adding extra water-insoluble components. Changing the surface area of the insert that contacts water during use of the oral irrigator can also change the rate of release.

The composite may also include a colorant that leaches from the composite at a rate corresponding to the rate of release of the substance. Thus, most of the colorant will have been released by the composite at about the same time most of the substance has been released. A user then can observe by the color change that the composite is used up.

The term "water", as used herein, encompasses pure water, housewater, and an aqueous solution, dispersion, etc. that include other components in addition to water.

The term "composite", as used herein, means a solid composition that includes a blend of the substance and at least one other chemically distinct component (e.g., a water insoluble polymer or a water-soluble polymer).

Other features and advantages of the invention will be apparent from the description of the preferred embodiments thereof, and from the claims.

BRIEF DESCRIPTION OF THE DRAWING

FIG. 2 is a tip for an oral irrigator.

FIG. 3 is a perspective view of a composite.

FIG. 4 is a cross-sectional view B of the composite, viewed along the longitudinal A axis.

DESCRIPTION OF THE PREFERRED EMBODIMENTS

Figure 1:
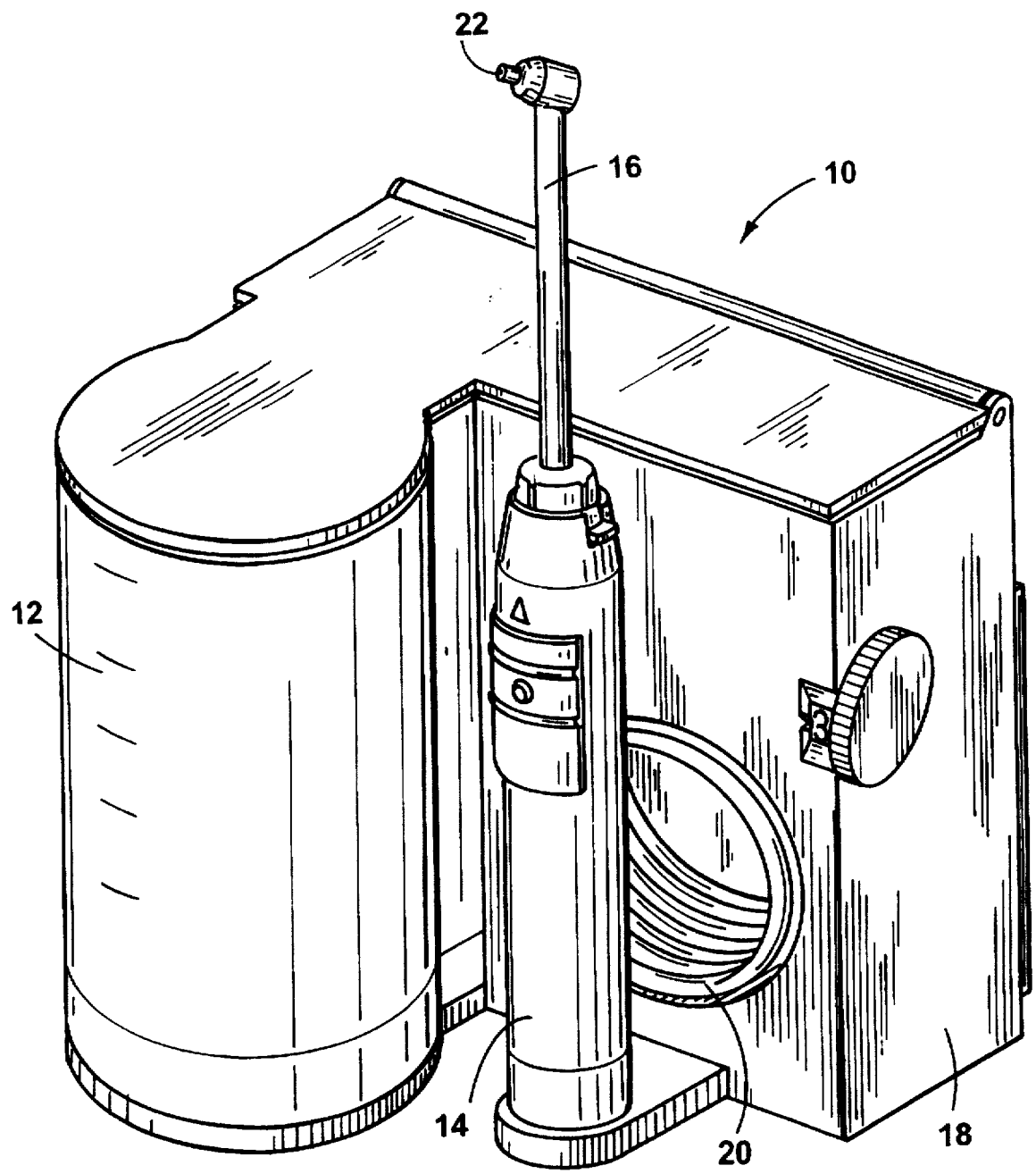
FIG. 1 is a perspective view of an oral irrigator.

Referring to FIG. 1 an oral irrigator 10 includes water source 12, a flow path (not shown), a hand-held portion 14 and a tip portion 16. Water from the water source 12 is forced through the housing 18 of the oral irrigator, through a tube 20 connecting the housing 18 to the tip portion 16. The water exits the tip portion at exit 22. Depicted is the commercially available Braun Oral-B Plak Control® Oral Irrigator, Model MD5000.

Referring to FIG. 2, the tip portion includes a fluid entrance 24, a fluid exit 22, and a shaft 26 connecting the fluid entrance and the exit. Locking clips 28 allows the tip portion to be detachably coupled to the oral irrigator. A molded or extruded composite (not shown in FIG. 2) is disposed in the fluid path of the tip portion.

Referring to FIGS. 3 and 4, the molded or extruded composite 29 is tube-shaped and includes a water insoluble support resin, a water-soluble polymer, a water-soluble monomeric species, and/or a polymer only swollen by water; and an antimicrobial agent, flavoring, whitener, fluoride compound, an anticalculus agent and/or foaming agent. The composite has an outer bore 30 and an inner bore 32. When inserted in the tip, water flows through the hollow center portion 34 of the composite, contacting the inner bore 32. The composite may be formed as a single unit with the tip portion, or it may be formed as a discrete unit so that it may be inserted and removed easily.

The water insoluble support resin can be, e.g., polystyrene, polyurethane, ethylene vinyl acetate (EVA), polyethylene, styrene/rubber, ethylene/propylene, or other acceptable, commercially available polymers. The water insoluble support resin is the backbone of the composite and has negligible solubility in water. It provides the composite with structural integrity when the other components of the composite leach out during use.

A sufficient amount, preferably greater than 25% by weight, of the water insoluble support resin should be included in the composite so that when other components leach out there is still enough resin present to maintain the structure of the composite. Of course, not so much should be included that the composite cannot be loaded with a sufficient amount of the other components. Preferably, the composite includes less than 90% by weight of the support resin.

A preferred support resin is EVA, which has low toxicity and is available in grades that have a low processing temperature. The preferred EVA includes between 5% and 50% by weight vinyl acetate. If the polymer includes too little vinyl acetate, the composite may be too stiff and require higher processing temperatures. If the polymer includes too much vinyl acetate, the composite may be rubber-like and too soft to process.

The water-soluble polymer can be, e.g., starches, polyvinyl alcohols, polyethylene oxides, hydroxyalkyl starches, hydroxyethyl and hydroxypropyl celluloses, polyacrylic acids, and gelatins. Most preferred are polyethylene oxides having a molecular weight between 100,000 and 5,000,000, e.g., Polyox® water-soluble resins, and polyacrylic acids, e.g., Carbopol® (available from the B. F. Goodrich Company).

Polyox water-soluble polymers are non-ionic ethylene oxide homopolymers that range in molecular weight from about 100,000 to 5,000,000. Polyox has a very low degree of toxicity, and grades are available that have a low processing temperature, and are completely water-soluble in cold and warm water.

The preferred Polyox, available from Union Carbide is WSR N-750, which has a molecular weight of 300,000. Alternatively, WSR N-80 (MW 200,000) can be used. WSR N-750 has a water solubility that is sufficient to provide a controlled release of the antimicrobial agent from the composite at bactericidal levels, but the solubility in the composite is low enough that it dissolves out slowly over a period of many uses.

A water-soluble monomeric species may be an organic compound or inorganic compound. Examples of organic compounds include fatty acids and carbohydrates. Examples of inorganic compounds include ammonium salts.

The composite preferably contains between 2% and 50% by weight, more preferably between 5% and 35% or 40%, of the water-soluble component. If too much is included, the antimicrobial agent may leach out too quickly, and the structural integrity of the composite once most of the polymer has leached out may be adversely affected. If too little is included, too low a quantity of the antimicrobial agent may be released from the composite during use.

A water-swellable polymer is a polymer which is relatively insoluble (less than 1000 ppm at 22° C.) in water but which can absorb at least 2 times its weight in water. Preferred water-swellable polymers can absorb 2 to 50 times their weight in water at 22° C. Commercially available polymers sometimes include small quantities of impurities, such as the starting materials used to synthesize the polymers, or uncross-linked polymers. The cross-linked polymers should be at least 99.9% pure when determining whether a particular polymer absorbs a sufficient quantity of water and is sufficiently insoluble in water to qualify as a water-swellable polymer.

Examples of water-swellable polymers include water-absorbing acrylics such as Salsorb 84, Salsorb 88, and Salsorb 90, all of which are available from Allied Colloids Corporation; cross-linked starch/sodium polyacrylate copolymers such as SanWet COS-960, SanWet COS-915, and SanWet COS-930, all of which are available from the Hoechst Celanese Corporation, and Waterlock A-180, which is available from Grain Processing Corporation; hydroxypropylmethylcelluloses such as Methocel, which is available from Dow Chemical Corporation; polyacrylic acids such as Carbopol 940, which is available from B.F. Goodrich Company; microcrystalline celluloses such as Avicel, which is available from FMC Corporation; chitosan pyrrolidone carboxylic acids such as Kytamer PC, which is available from Amerchol Corporation; acrylic acid/acrylonitrogen copolymers such as Hypan-SA-100H, which is available from Kingston Hydrogels Corporation; cross-linked potassium acrylates such as Liqua-Gel, which is available from Miller Chem. & Fertilizer Corporation; carboxymethylcelluloses such as Aquasorb B-315 (Na salt) and AQU-D3236 (Al/Na salt), both of which are available from Aqualen Corporation; and cross-linked polyacrylic acid polyalcohol grafted copolymers such as FAVOR SAB 800, which is available from Stockhausen Company. Two further examples of water-swellable polymers are Ultrasponge (available from MicroVesicular Systems Inc.), and Costech (available from Costech Corporation). The more preferred water-swellable polymers are the SanWets and Salsorbs.

A sufficient quantity of the water-swellable polymer should be included in the composite such that, when the composite is contacted with water, the swelling of the polymer causes an increase in the release of the substance from the composite. When water-swellable polymers are used, the composite preferably includes between 0.2% to 50%, more preferably between 3% and 15%, and most preferably between 4% and 8%, of the water-swellable polymer by weight.

Examples of substances that can be included in the composite for eventual release include antimicrobial agents, flavorants, whiteners, fluoride compounds, foaming agents, desensitizing agents, nutritional agents, odor-preventing agents, remineralizing agents, anticalculus agents, antiinflammatory agents, salivary gland stimulators, antifungal agents, and antiviral agents. The amount of a particular substance included in the composite depends on the level of the desired dosage, which is itself dependent on the amount of water-soluble polymer; the composite may include, for example, between 1% and 40% (or even between 1% and 60%) of the substance by weight. If too high a level of the substance is included, the composite may become brittle. Of course, a sufficient amount of the substance should be included so that enough is released during use to cause the desired result.

Examples of antimicrobial agents that can be used in the composite include bisguanides such as chlorhexidine and alexidine; quaternary ammonium compounds such as cetylpyridinium chloride, domiphen bromide, and benzalkonium chloride; zinc salts such as zinc chloride and zinc citrate; antibiotics such as chlortetracycline, tetracycline, actinobolin, streptomycin, kanamycin, neomycin, niddamycin, bacitracin, erythromycin, penicillin, rancemycin, gramicidin, saramycin, and polymixin B; as well as antiplaque enzymes such as mucinases, pancreatin, fungal enzymes, protease-amylase, dextranase, moimnase, zendium, amyloglucosidase, and glucose oxidase. The preferred antimicrobial agents for use in the composite are chlorhexidine and triclosan. When chlorhexidine is used, it is preferred to use its digluconate salt; the hydrochloride and diacetate salts can also be used.

Examples of flavorants include, e.g., peppermint, spearmint, or cinnamon, added as oils or compounded with structural plastic (e.g., PolyIff®). These flavorants are available from International Flavors and Fragrances (IFF).

Examples of whiteners include hydrogen peroxide, peroxyborate monohydrate, and other peroxy compounds.

Examples of fluoride compounds include sodium fluoride, alkylammonium fluorides, stannous fluoride, sodium monofluorophosphate, etc.

Examples of foaming agents include surfactants like various Pluronics, which are available from BASF, and Tween.

Examples of desensitizing agents include strontium chloride, strontium citrate, calcium oxalate, potassium nitrate, and potassium oxalate.

Examples of nutritional agents include Vitamin C and Vitamin E.

Examples of odor-preventing agents include zinc salts (e.g., zinc chloride and zinc citrate) and chlorophyll compounds.

Examples of remineralizing agents include various calcium/phosphate systems.

Examples of anticalculus agents include zinc salts (e.g., zinc chloride and zinc citrate), tetrasodium pyrophosphate, and disodium dihydrogen pyrophosphate.

Examples of anti-inflammatory agents include steroids (e.g., triamcinolone diacetate), salicylates (e.g., acetylsalicylic acid), and hormones (e.g., cortisone acetate).

Examples of salivary gland stimulators include citric acid and pilocarpine.

Examples of antifungal agents include nystatin, econazole nitrate, and clotrimazole.

Examples of antiviral agents include AZT and trifluridine.

The composite may include other ingredients like dispersing agents (e.g., glycerol distearate) that can help provide a more uniform distribution of the substance throughout the composite. The composite may include, e.g., from 2% to 8% dispersing agent by weight.

An example of a composite including 51% by weight EVA as the water-insoluble support resin, 40% by weight chlorhexidine digluconate, and 9% by weight Carbopols (a preferred water-soluble polymer) was prepared according to the following procedure.

MATERIALS a. Chlorhexidine Digluconate

A 20 percent solution of chlorhexidine digluconate, available from Pliva Pharmaceutical, Chemical, Food and Cosmetic Industry of Zagreb, Yugoslavia, or ICI, was freeze-dried as follows:

1. Measure 500 ml of chlorhexidine digluconate in a graduated cylinder and transfer it to a liter flask.
2. Adjust volume to 1 liter with double distilled filtered water and mix together.
3. Transfer 300 ml. portions of mixture to glass evaporating dishes (8 inch diameter).
4. Place all evaporating dishes in the freeze-drying apparatus until all water is removed.
5. Transfer the chlorhexidine freeze-dried powder to a 1 liter glass bottle and cap.
6. Store the bottle in a refrigerator or a dark room at approximately 4° C.

Optionally, chlorhexidine digluconate can be bought already freeze-dried from Pliva.

b. Ethylene Vinyl Acetate

The most preferred ethylene vinyl acetate is sold by DuPont under the tradename ELVAX 360, and has a vinyl acetate content of 25 percent by weight; a tensile strength of 18.0 Mpa at 23° C. (ASTM D638); an elongation of 800 percent at 23° C. (ASTM D638); a softening temperature of 53° C. (ASTM D1525); and a flexural modulus of 26 Mpa at 23° C. (ASTM D790). ELVAX 360 contains 500 ppm BHT as an anti-oxidant.

In order to mix with chlorhexidine and Carbopol®, ELVAX 360 pellets are ground into powders with particle sizes of less than 250 microns with a Glen Mill Granulator (Model #CS 150/100-2) installed with a screen plate having 1 mm screen holes. A suction system is added to the grinding chamber to facilitate the removal of powders from the chamber to a container. During grinding, the material is recycled through the grinder as many times as necessary (usually two or three passes) to meet the size requirement.

A sieve shaker manufactured by the W.S. Tyler Co. is used to control the sizes as needed.

c. Carbopol®

Carbopol® 934PNF, pharmaceutical grade, is available from B.F. Goodrich Company. The Carbopol® is used as received and mixed with other components to form the composite.

d. Blending of Materials

The ELVAX 360, Carbopols®, and chlorhexidine digluconate are mixed in a blender. Each component is first weighed and then poured into a glass jar with a capacity of 0.5 kilograms. The jar is then placed on a ball-mill rotator and mixed for approximately ½ hour. For a quantity greater than 0.5 kilograms, a V-blender manufactured by Patterson-Kelly Co. Inc. is used. The blended material should be stored in a dry, cool room.

e. Processing

The conventional equipment that can be used to produce the composite includes an extruder, a cooling plate, a puller, and an extrusion die. Each die is supplied with a sensor for the recording of melt pressure and temperature. Pulling speed is adjusted to produce the appropriate sample.

Samples can be made with either a twin-screw or a single-screw extruder. The Werner & Pfleiderer 30 mm twin-screw extruder is based on a corotating and intermeshing twin-screw system. To minimize degradation during processing, the twin-screw extruder consists of only two high-shear kneading elements and the rest being low-shear conveying screw elements; the screw speed and processing temperatures are reduced to a minimum. The mixture is fed using a K-tron twin-screw feeder (Model T-20).

Alternatively, a Haake ¾ inch single-screw extruder equipped with a 5 HP drive motor is employed. When making the most preferred composite, the extruder was operated with a screw speed of 35 rpm, a barrel pressure of 70 psi, a die pressure of 80 psi, a barrel temperature of 113° C., and a die temperature of 113° C.

The blend of materials is fed to either extruder and the tube produced is pulled onto a rod. The tube is cooled by blowing dry compressed air into the tube. The finished product should be kept in a cool, dry room.

The composites can also be made by other conventional processes, such as by injection molding, compression molding, thermforming, and casting.

A composite prepared as described above was inserted in the tip portion and connected to the oral irrigator. The irrigator was charged with 250 ml of water and allowed to run (at a speed of 5) until all of the water had passed through the inner bore of the composite in the tip portion. Water contacts the composite and dissolves the Carbopolm polyacrylic acid. Channels form within the support, causing the chlorhexidine to be released into the flow path. The solution was collected and analyzed for its chlorhexidine content. Repeatedly, 3 mg (+/−1 mg) of chlorhexidine was present in the solution. Thus, a steady release of chlorhexidine was achieved. After 28 consecutive trials, no significant amount of chlorhexidine was detected. When the chlorhexidine is expired, the composite (or the entire tip) may be replaced.

Other embodiments are within the claims. For example, the composite can be shaped as a tapered tube, instead of the straight tube illustrated in the figures. Moreover, the central opening through the tube can be, e.g., star shaped to provide more surface area for water contact. Similarly, the outer surface of the tube can have ridges so that when the tube is positioned in the flow path water can pass through channels between the exterior surface of the composite and the wall defining the flow path. Composites having other shapes, e.g., a flat strip, can be positioned in the flow path and used in place of or in combination with a tube-shaped composite.

In addition, the composite itself can be formed of more than one layer. Each layer, for example, may include a different substance for release in response to contact with water. Further, the substance to be released may be microencapsulated. This can provide increased ease of processing, particularly when processing involves high temperature.

The composite also may include the substance to be released and a water-soluble polymer, but not include a water-insoluble support resin. The composite may include, for example, between 1% and 99% (or between 10% and 99% or between 30% and 90%) of the substance by weight and between 1% and 99% (or between 10% and 99%, or between 30% and 90%) of the water-soluble polymer by weight. The water-soluble polymer dissolves over time when the composite is contacted with water. An advantage of a composite including the substance and a water-soluble polymer is that a high quantity (e.g., 80% or more) of the substance can be included in the composite. For example, the composite may include 90% chlorhexidene digluconate and 10% Polyox® compression molded at ambient temperatures into the desired shape. The composite may also include, for example, 35% chlorhexidene diglucanate and 65% Polyox®. The composite can be inserted into or otherwise be surrounded by a support layer made, for example, of a plastic material.

In another embodiment, the water irrigator may include more than one composite each, including a substance (the same or different) that is released when the composites are contacted with water.

In another embodiment, the insert for the tip or irrigator consists only of the bisguanide or a quaternary ammonium compound.

We claim:

1. An oral irrigator for delivering a substance to the mouth when water flows through the irrigator, said irrigator comprising:
   a tip portion for dispensing water into the mouth;
   a flow path that delivers water through said irrigator, including said tip portion, to said mouth; and
   a composite comprising a blend of a polymer and a substance that is released from the composite when the composite is contacted with water, positioned in said irrigator so that water flowing through said irrigator contacts said composite.

2. The oral irrigator of claim 1 wherein said composite is positioned in said tip portion.

3. The oral irrigator of claim 2 wherein said composite is tube-shaped and has an opening through which water can pass.

4. The oral irrigator of claim 1 wherein said substance is an antimicrobial agent.

5. The oral irrigator of claim 4 wherein said antimicrobial agent is chlorhexidine.

6. The oral irrigator of claim 1 wherein said substance is selected from the group consisting of tooth whiteners, flavorants, fluoride-containing compounds, foaming agents, desensitizing agents, nutritional agents, odor-preventing agents, remineralizing agents, anticalculus agents, anti-inflammatory agents, salivary gland stimulators, antifungal agents, and antiviral agents.

7. The oral irrigator of claim 1 wherein said composite further comprises a water insoluble polymer.

8. The oral irrigator of claim 7 wherein said composite further comprises a release-enhancing material comprising a water-soluble or water-swellable material.

9. The oral irrigator of claim 8 wherein said release-enhancing material comprises a water-soluble polymer.

10. The oral irrigator of claim 9 wherein said water-soluble polymer comprises a polymer selected from the group consisting of polyethylene oxide and polyacrylic acid.

11. The oral irrigator of claim 9 wherein said substance comprises an antimicrobial agent and wherein said composite comprises from 25 to 90 percent by weight water-insoluble polymer, from 5 to 40 percent by weight water-soluble polymer, and from 1 to 60 percent by weight antimicrobial agent.

12. The oral irrigator of claim 11 wherein said antimicrobial agent comprises chlorhexidine.

13. The oral irrigator of claim 1 wherein said composite further comprises a water-soluble polymer.

14. The oral irrigator of claim 13 wherein said substance comprises an antimicrobial agent.

15. The oral irrigator of claim 14 wherein said antimicrobial agent comprises chlorhexidine.

16. A tip suitable for attachment to an oral irrigator, said tip comprising:
a body including a water entrance, a water exit, a flow path connecting said entrance and said exit, and a composite comprising a polymer and a substance that is released from said composite for delivery to a mouth when said composite is contacted with water,
said composite being positioned in said tip so that water flowing through said flow path contacts said composite.

17. The tip of claim 16 wherein said composite is tube-shaped and is located in said flow path.

18. The tip of claim 16 wherein said substance comprises an antimicrobial agent.

19. The tip of claim 18 wherein said antimicrobial agent comprises chlorhexidine.

20. The tip of claim 16 wherein said composite further comprises a water-soluble polymer.

21. The tip of claim 20 wherein said substance comprises chlorhexidine.

22. The tip of claim 16 wherein said composite further comprises a water insoluble polymer.

23. The tip of claim 22 wherein said composite further comprises a release enhancing agent selected from the group consisting of water-soluble polymers and water-swellable polymers.

24. The tip of claim 23 wherein said release-enhancing material is a water-soluble polymer.

25. The tip of claim 24 wherein said water-soluble polymer comprises a polymer selected from the group consisting of polyethylene oxide and polyacrylic acid.

26. The tip of claim 24 wherein said substance is an antimicrobial agent and wherein said composite comprises from 25 to 90 percent by weight water-insoluble polymer, from 5 to 40 percent by weight water-soluble polymer, and from 1 to 60 percent by weight antimicrobial agent.

27. The tip of claim 26 wherein said antimicrobial agent comprises chlorhexidine.

28. The tip of claim 16 wherein said substance is selected from the group consisting of tooth whiteners, flavorants, fluoride-containing compounds, foaming agents, desensitizing agents, nutritional agents, odor-preventing agents, remineralizing agents, anticalculus agents, anti-inflammatory agents, salivary gland stimulators, antifungal agents, and antiviral agents.

29. A method of introducing a substance into a mouth, comprising flowing water into contact with a composite and then into said mouth, said composite comprising a blend of a polymer and a substance that is released from said composite when water contacts said composite, said substance being released from said composite when contacted with flowing water and carried by said flowing water into said mouth.

30. The method of claim 29 wherein said composite further comprises a water-insoluble polymer.

31. The method of claim 29 wherein said composite further comprises a water-soluble polymer.

32. The method of claim 29 wherein said composite is extended or molded prior to flowing water into contact with said composite to release the substance into the mouth.

33. An oral irrigator for delivering a substance to the mouth when water flows through the irrigator, said irrigator comprising:
a tip portion for dispensing water into the mouth;
a flow path that delivers water through said irrigator, including said tip portion, to said mouth; and
a composite comprising a polymer and a compound selected from the group consisting of bisquanides and quaternary ammonium compounds positioned in said irrigator so that water flowing though said irrigator contacts said compound.

34. A tip suitable for attachment to an oral irrigator, said tip comprising:
a body including a water entrance, a water exit, a flow path connecting said entrance and said exit, and a composite comprising a polymer and a compound selected from the group consisting of bisquanides and quaternary ammonium compounds positioned in said tip so that water flowing through said flow path contacts said compound.

35. An oral irrigator for delivering a substance to the mouth when water flows through the irrigator, said irrigator comprising:
a tip portion for dispensing water into the mouth;
a flow path that delivers water through said irrigator, including said tip portion, to said mouth; and
a composite comprising a substance that is released from the composite when the composite is contacted with water, positioned within said tip portion of said irrigator so that water flowing through said irrigator contacts said composite, said composite being tube-shaped and having an opening through which water can pass.

36. An oral irrigator for delivering a substance to the mouth when water flows through the irrigator, said irrigator comprising:
a tip portion for dispensing water into the mouth;
a flow path that delivers water through said irrigator, including said tip portion, to said mouth; and
a composite comprising a water insoluble polymer, a release-enhancing material comprising a water-soluble or water-swellable material, and a substance that is released from the composite when the composite is contacted with water, said composite being positioned in said irrigator so that water flowing through said irrigator contacts said composite.

37. The oral irrigator of claim 36 wherein said release-enhancing material comprises a water-soluble polymer.

38. The oral irrigator of claim 37 wherein said water-soluble polymer comprises a polymer selected from the group consisting of polyethylene oxide and polyacrylic acid.

39. The oral irrigator of claim 37 wherein said substance comprises an antimicrobial agent and wherein said composite comprises from 25 to 90 percent by weight water-insoluble polymer, from 5 to 40 percent by weight water-soluble polymer, and from 1 to 60 percent by weight antimicrobial agent.

40. The oral irrigator of claim 39 wherein said antimicrobial agent comprises chlorhexidine.

41. A tip suitable for attachment to an oral irrigator, said tip comprising:

a body including a water entrance, a water exit, a flow path connecting said entrance and said exit, and a composite comprising a substance that is released from said composite for delivery to a mouth when said composite is contacted with water, said composite being tube shaped and being positioned in said flow path so that water flowing through said flow path contacts said composite.

42. The tip of claim 41 wherein said composite further comprises a release enhancing agent selected from the group consisting of water-soluble polymers and water-swellable polymers.

43. The tip of claim 42 wherein said release-enhancing material is a water-soluble polymer.

44. The tip of claim 43 wherein said water-soluble polymer comprises a polymer selected from the group consisting of polyethylene oxide and polyacrylic acid.

45. The tip of claim 43 wherein said substance is an antimicrobial agent and wherein said composite comprises from 25 to 90 percent by weight water-insoluble polymer, from 5 to 40 percent by weight water-soluble polymer, and from 1 to 60 percent by weight antimicrobial agent.

46. The tip of claim 45 wherein said antimicrobial agent comprises chlorhexidine.

47. An oral irrigator for delivering a substance to the mouth when water flows through the irrigator, said irrigator comprising:

a tip portion for dispensing water into the mouth;

a flow path that delivers water through said irrigator, including said tip portion, to said mouth; and a composite comprising a polymer and a substance that is released from the composite when the composite is contacted with water, positioned in said tip portion so that water flowing through said irrigator contacts said composite.

48. The oral irrigator of claim 47 wherein said composite is tube-shaped and has an opening through which water can pass.

49. An oral irrigator for delivering a substance to the mouth when water flows through the irrigator, said irrigator comprising:

a tip portion for dispensing water into the mouth;

a flow path that delivers water through said irrigator, including said tip portion, to said mouth; and a composite comprising a polymer and an antimicrobial agent that is released from the composite when the composite is contacted with water, said composite being positioned in said irrigator so that water flowing through said irrigator contacts said composite.

50. The oral irrigator of claim 49 wherein said antimicrobial agent is chlorhexidine.

51. An oral irrigator for delivering a substance to the mouth when water flows through the irrigator, said irrigator comprising:

a tip portion for dispensing water into the mouth;

a flow path that delivers water through said irrigator, including said tip portion, to said mouth; and a composite comprising a polymer, a water insoluble polymer, a substance that is released form the composite when the composite is contacted with water, and a release-enhancing material comprising a water-soluble or water-swellable material, said composite being positioned in said irrigator so that water flowing through said irrigator contacts said composite.

52. The oral irrigator of claim 51 wherein said release-enhancing material comprises a water-soluble polymer.

53. The oral irrigator of claim 52 wherein said water-soluble polymer comprises a polymer selected from the group consisting of polyethylene oxide and polyacrylic acid.

54. The oral irrigator of claim 52 wherein said substance comprises an antimicrobial agent and wherein said composite comprises from 25 to 90 percent by weight water-insoluble polymer, from 5 to 40 percent by weight water-soluble polymer, and from 1 to 60 percent by weight antimicrobial agent.

55. The oral irrigator of claim 54 wherein said antimicrobial agent comprises chlorhexidine.

56. An oral irrigator for delivering a substance to the mouth when water flows through the irrigator, said irrigator comprising:

a tip portion for dispensing water into the mouth;

a flow path that delivers water through said irrigator, including said tip portion, to said mouth; and a composite comprising a polymer, a water-soluble polymer, and a substance that is released from the composite when the composite is contacted with water, said composite being positioned in said irrigator so that water flowing through said irrigator contacts said composite.

57. The oral irrigator of claim 56 wherein said substance comprises an antimicrobial agent.

58. The oral irrigator of claim 57 wherein antimicrobial agent comprises chlorhexidine.

59. A method of introducing a substance into the mouth, comprising flowing water into contact with a composite and then into said mouth, said composite comprising a polymer, a water-soluble polymer and a substance that is released from said composite when water contacts said composite, said substance being released from said composite when contacted with flowing water and carried by said flowing water into said mouth.

* * * * *